United States Patent [19]

Nadal

[11] Patent Number: 5,383,887
[45] Date of Patent: Jan. 24, 1995

[54] DEVICE FOR SELECTIVELY FORMING A TEMPORARY BLOOD FILTER

[75] Inventor: Guy Nadal, Poitiers, France

[73] Assignee: Celsa LG, Chasseneuil, France

[21] Appl. No.: 174,358

[22] Filed: Dec. 28, 1993

[30] Foreign Application Priority Data

Dec. 28, 1992 [FR] France .................. 92 15774

[51] Int. Cl.⁶ .................. A61F 2/02; A61B 17/00
[52] U.S. Cl. .................. 606/200; 606/198
[58] Field of Search ........... 606/108, 194, 195, 198, 606/200; 604/104, 106; 623/1

[56] References Cited

U.S. PATENT DOCUMENTS

| | | | |
|---|---|---|---|
| 4,580,568 | 4/1986 | Gianturco | 604/96 |
| 4,650,466 | 3/1987 | Luther | |
| 4,817,600 | 4/1989 | Herms et al. | 606/200 |
| 5,035,706 | 7/1991 | Giantureo | 606/198 |
| 5,059,205 | 10/1991 | El-Nounou et al. | 606/200 |

FOREIGN PATENT DOCUMENTS

| | | |
|---|---|---|
| 0348295 | 12/1989 | European Pat. Off. |
| 0423916A1 | 4/1991 | European Pat. Off. |
| 0466518A3 | 1/1992 | European Pat. Off. |
| 2657261 | 7/1991 | France |
| 8812719.2 | 12/1989 | Germany |
| WO92/1931-01 | 11/1992 | WIPO |
| 9313825 | 7/1993 | WIPO .................. 606/198 |

*Primary Examiner*—Ralph A. Lewis
*Attorney, Agent, or Firm*—Pollock, Vande Sande & Priddy

[57] ABSTRACT

The invention relates to a device which can be implanted inside a vessel to form a blood filter there. The device comprises a structure (7) disposed along the axis (3) of a surface of revolution, radially to which axis the structure can be expanded or compressed such that, in its expanded position, it can contact the interior of the vessel. Means (15, 17) for stressing at least a portion of this structure "in situ" are further provided either to move it closer to the axis of the surface of revolution, forming a constriction area for filtering the blood, or to move it away therefrom, thus varying this filtering capacity. Application to temporary filters which can be implanted "for life".

10 Claims, 3 Drawing Sheets

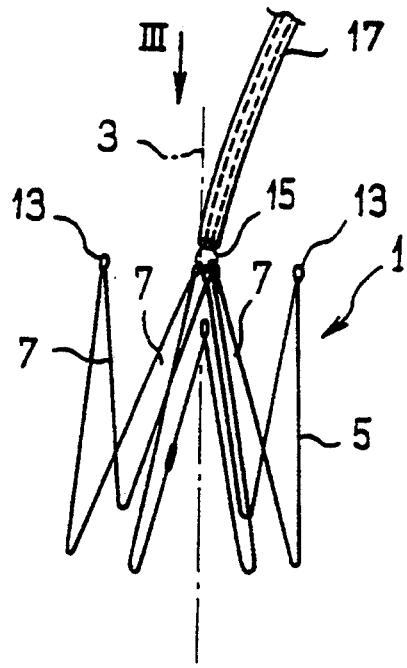
FIG_1
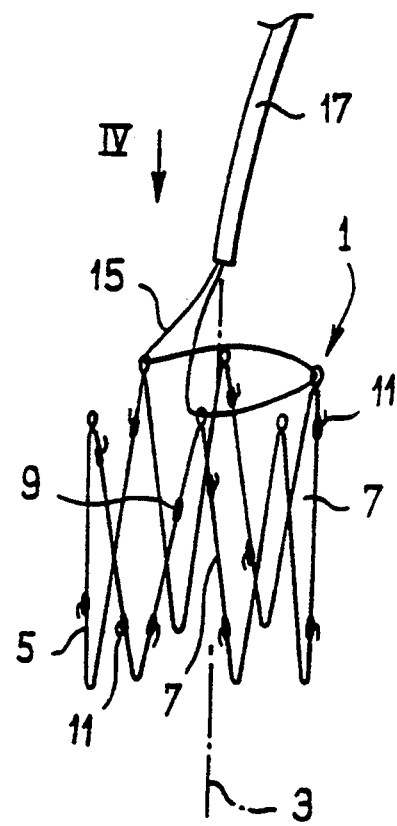
FIG_2
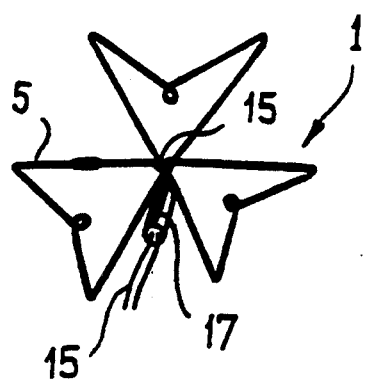
FIG_3
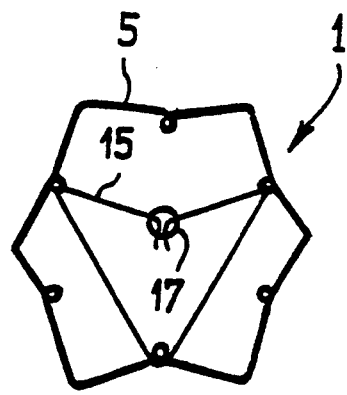
FIG_4

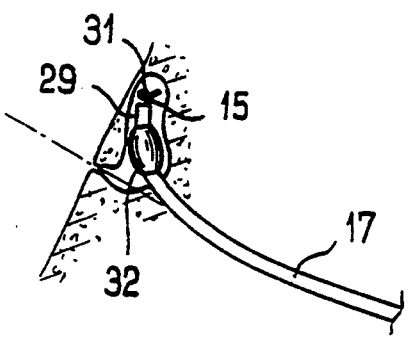
FIG_7
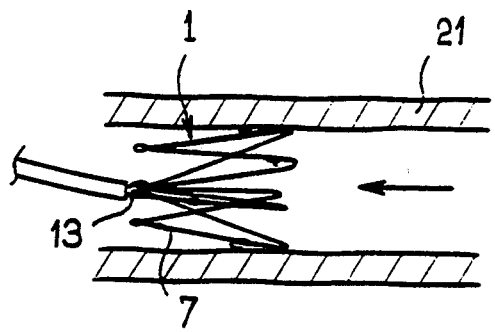
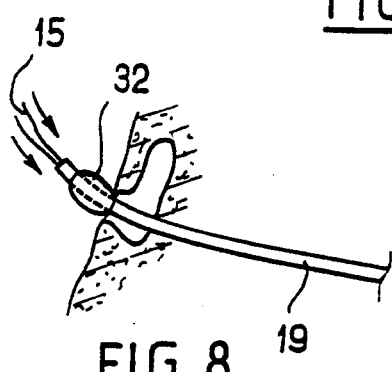
FIG_8
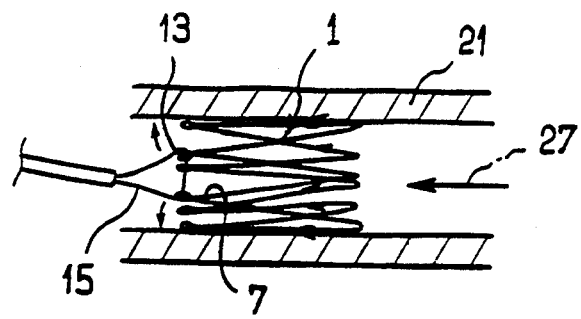
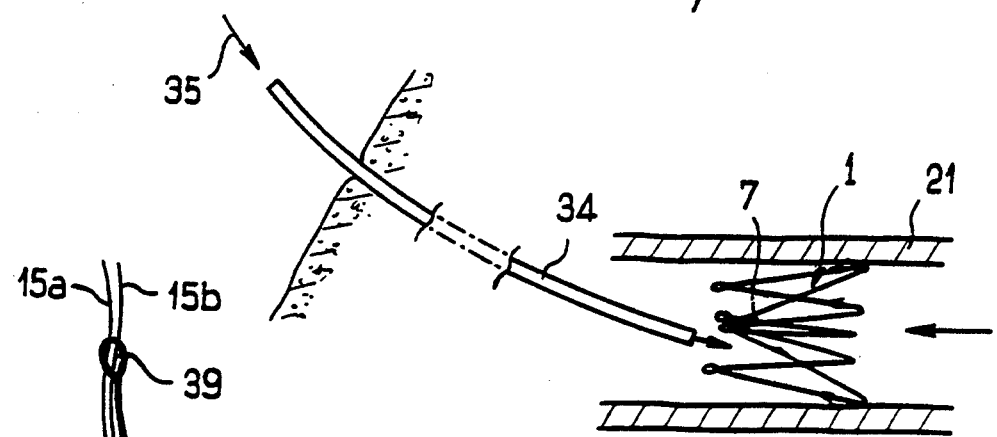
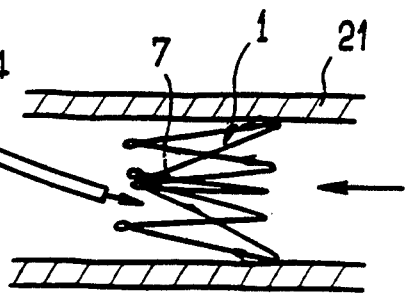
FIG_9
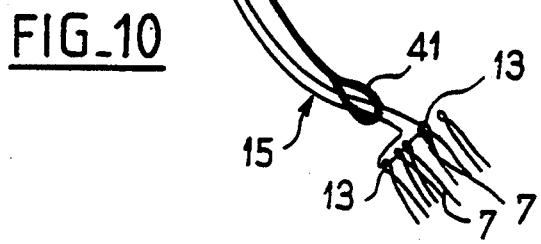
FIG_10

DEVICE FOR SELECTIVELY FORMING A TEMPORARY BLOOD FILTER

FIELD OF THE INVENTION

The invention relates to devices which can be implanted inside a vessel in order to form a blood filter there which can be temporary.

BACKGROUND OF THE INVENTION

Filters of this type are frequently intended to be installed in the vena cava, such as the inferior vena cava, in particular percutaneously.

It has been known for many years that filters which are left indefinitely can, in the long-term, cause considerable complications for the patient, such as obstructions of the vessel in which the filter is implanted and side-effects in the veins.

Today, these side-effects are accepted, in particular when there is a constant risk of pulmonary embolism during the course of time.

Nevertheless, it has appeared desirable to be able to remove a "barrier" of this type, in particular, whenever the risk of the embolism recurring no longer creates a danger for the invalid.

Current temporary filters have this ability to be installed to provide protection only for the necessary amount of time and then of being removed.

Several categories of temporary filters exist already or are in the process of development, among which can be cited:

filters of which the filtering element rests on a catheter emerging from the patient's body at the location of the aperture which is provided through the skin and from which the access route to the vessel extends. In practice, these devices cannot be left in place for more than a fortnight owing to the risks of infection associated with the catheter outlet. Thus, they are usually used for medical action providing short-term protection, such as thrombolysis operations for clots in the vessels.

Filters can also be cited of which the filter element rests on a catheter which is kept implanted under the skin, similar to the device described in patent application FR-A-2 657 261. These filters can be used for a longer duration since the risk of infection is very largely limited, or even eliminated. Nevertheless, implantation is restricted in terms of time, even though this may be a period of several weeks, in so far as, in practice, the vessel walls and the filter adhere to one another during the course of time. It may even occur that the filter can no longer be withdrawn without damaging the vessel.

A third category of filter concerns those of which the filter element is made from a material which has the capacity to be absorbed over time, such as the one proposed in patent application FR-A-2 689 388. The length of use thus depends on the speed at which the material is absorbed in the blood. Although numerous research teams are working on the subject, the Applicants are not aware of any filter of this type being currently available, however, in view of the problems of mastering the absorption process in particular.

This brief survey shows that, at present, to the Applicants' knowledge, no equipment exists which enables the blood to be filtered "in situ" for a given period of time, possibly for more than several months, without the patient having to suffer the long-term complications of the current definitive filters which can be left in place for life.

BRIEF DESCRIPTION OF THE PRESENT INVENTION

The object of the invention is to propose a device which overcomes these problems.

To this end, the device of the invention which can thus constitute a temporary blood filter comprises:

an open structure which defines a tubular surface having a tube axis and through which the blood can pass, this tubular structure having a first, small tube diameter, for its implantation as far as said vessel, and a second, expanded tube diameter so as to be suitable for contacting this vessel radially in a position in which it is implanted therein;

and means for stressing this structure, when the latter comprises its second, expanded tube diameter in order:

either for at least a portion of this structure to move closer to its axis such that a constriction area corresponding to a filtering position suitable for retaining clots which may be present in the blood passing through the structure is formed;

or, from this so-called filtering position, to move the portion of the structure defining this constriction area away from its axis, such that the filtering capacity of the device is varied.

In this way, it is possible to adapt the filtering duration practically at will, while developing the filtering capacity of the device according to requirements, without necessarily having to remove the device once it has fulfilled its filtering role.

As an option, it is even possible to envisage varying the filtering role of the device periodically.

In view of the fact that the device need no longer be removed in order to stop filtering the blood, the device could, consequently, be left "for life", without account having to be taken of parameters concerning infection or adherence to the vessel walls during the course of time.

In order to be efficient, according to a further characteristic, the device of the invention is such that in the "filtering" position, the above portion of the structure which is subject to stress advantageously defines substantially a cone or a truncated cone, while, in the radially spaced position, this same portion of the structure preferably defines a truncated cone, which is relatively slightly flared, or a cylinder.

In order to provide the greatest possible degree of safety, outside the area which is to be stressed, the structure in question is further provided with attachments means, such as hooks, for securing it to the vessel wall. Thus, the possible risks of migration are very greatly reduced, once the device is implanted.

Given that, apart from the case in which means of stressing the portion of the structure which can be absorbed over time are provided, in practice the practitioner must be able to act on this implanted structure, and remote means for controlling these stressing means are therefore advantageously included.

Thus, it is in particular possible for the practitioner to act, without large-scale surgical intervention, from the exterior of the patient's body, using the route already provided for access to the vessel for this purpose.

The use of thin surgical forceps which can slide through the patient's body to the area where the device is implanted can in particular be used as the remove-control means, and these forceps can then be used to cut a surgical thread forming the means for retaining the portion of the structure in question in the close-together position, which portion, once the thread has been cut, can naturally expand if it is made of a radially expanding, elastically deformable structure.

As a variant, the use of a thin catheter through which a wire having a loop suitable for passing through apertures provided in the structure can pass towards the location from which the cross-section is to be altered, can further be envisaged as a remote-control means. In this case, the proximal end of this catheter closest to the surface of the skin can even be lodged subcutaneously without emerging at all from the patient's body between two insertions, as is described in patent applications FR-A-2 657 261, or FR-92 13909 of Nov. 19, 1992.

If an implantable injection chamber is provided, it is further possible to diffuse a treatment product whenever necessary at the location of the filter.

Further characteristics and advantages of the invention will become clear from the following description given with reference to the attached drawings which are provided purely by way of non-limiting example and in which:

BRIEF DESCRIPTION OF THE FIGURES

FIG. 1 shows a preferred alternative embodiment of the device according to the invention, here illustrated in the filtering position;

FIG. 2 shows the same device in the non-filtering position;

FIGS. 3 and 4 show respectively the device of FIGS. 1 and 2 in plan view, in the directions of the arrows III and IV of FIGS. 1 and 2;

FIGS. 5 to 8 show different stages of implantation (FIGS. 5 and 6) or of use (FIGS. 7 and 8) of the device illustrated in the preceding Figures; and FIGS. 9 and 10 each show an alternative embodiment of the remote means for controlling the modification of the radial cross-section of the device.

DETAILED DESCRIPTION OF THE INVENTION

Figure 5:
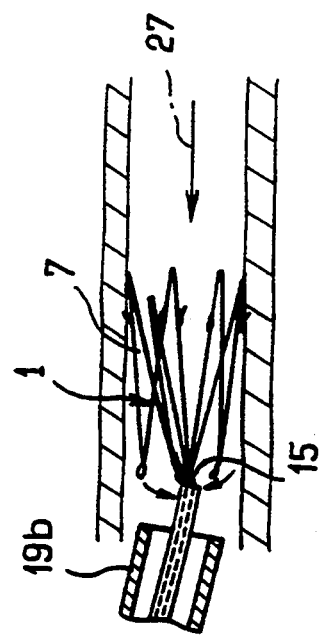
Figure 6:
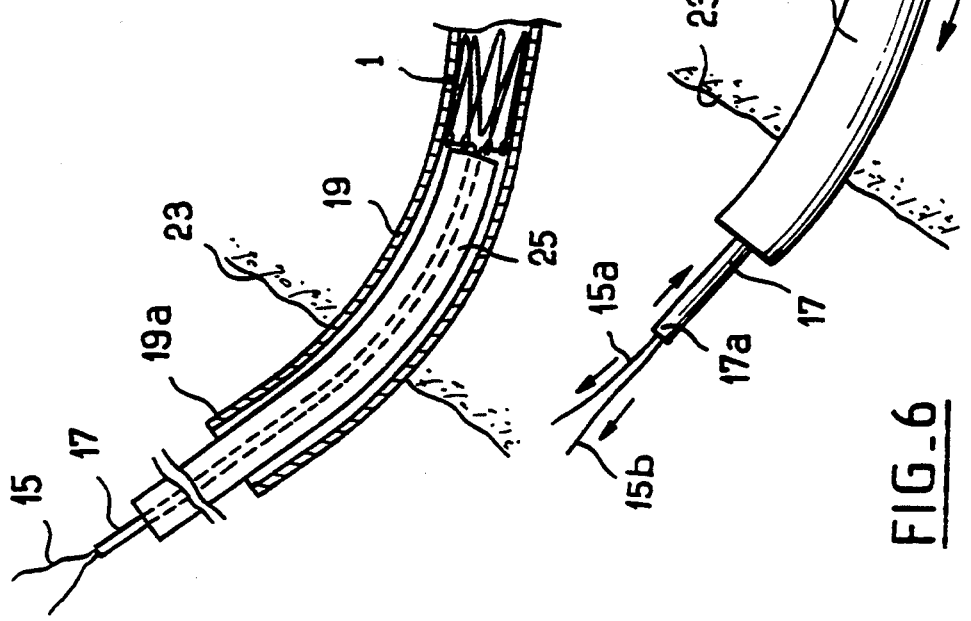

FIGS. 1 to 4, first of all, illustrate a device 1 for performing, at least temporarily, the function of a blood filter which can intercept any clots which may be circulating in this blood.

In this case, the monobloc device is in the form of a structure which can automatically expand radially to its axis 3 such that, when it has been released in the required vessel, it is centered substantially on the axis of this vessel.

As can be seen, the structure 1 here consists of a thread 5, which is preferably round and is relatively rigid, shaped in a zig-zagged manner in the general direction of the axis 3 and wound up on itself so as to form a closed configuration which, in this instance and in its unstressed position shown in FIG. 2, defines a tubular surface with a substantially cylindrical (or slightly frustoconical) wall suitable to be placed firmly against the internal wall of the selected vessel via these V-shaped finger portions 7.

The area in which the thread is closed and where its ends join is indicated 9.

Once it has been implanted, a structure of this type provides a large surface area in contact with the vessel wall against which the curved end portions and/or lines of the thread extending between each other substantially bear. In this case, the "open", tubular wall of the structure 1 is thus formed of a series of filamentary fingers which are extended essentially substantially along the axis 3 and arranged such that blood can pass between them but which are sufficiently tight to retain any clots.

Advantageously, small hooks 11 for attachment to the vessel wall further restrict the risks of the device migrating. These hooks can project slightly from plates welded to the lines forming the zigzag and can extend in pairs in opposite directions.

However, in practice, these hooks are preferably not provided on some of the fingers 7, given that, as FIG. 1 shows, some of these fingers (for example, one out of two) are provided such that they can be moved close to one another towards the axis 3, thus substantially forming a cone or a relatively closed truncated cone, and therefore locally constricting the cross-section of at least part of the device such that it can completely fulfil its role of blood filter.

In order to control the variation of the cross-section, it is provided that at least some of the fold areas of the thread be formed as a loop 13, at at least one of the axial ends of the structure.

A thread 15 is passed inside the passage defined by one loop out of each two.

As a result of this tie being tightened to a greater or lesser extent, it is possible to change at will from the shape shown in FIGS. 1 and 3 to that shown in FIGS. 2 and 4.

It will be appreciated that this tie can be used alone.

Whereas the zigzagged structure 1 is advantageously made of metal a few tenths of a millimeter in cross-section, for example, of cobalt steel (usually known by the registered trademark of PHYNOX), the filament 15 can be made of a cuttable screen which is biocompatible or possibly biodegradable such that it can then be absorbed on contact with blood.

In the latter case, polyglycolic acid or polylactic acid can be used in particular.

A further solution consists of in using a surgical thread, which cannot be biologically absorbed, passing it in a loop through the selected loops 13, and moving its two, opposite ends up through a thin, flexible catheter 17 which can advance along the access route connecting the puncture point provided in the skin to the implantation area in the vessel, thus enabling the tightening or releasing of the tie 15 to be controlled from the exterior of the patient's body and thus the filtering capacity of the device to be varied.

With reference to FIGS. 5 to 8, one possible method of implanting and using the device 1 will now be described in brief, the device being implanted under, at least local, anaesthetic.

However, it will noted at this stage that the device is implanted in a conventional manner known per se, for example as described in patent application FR92 13909.

Firstly, the operator can commence by providing in the neck a percutaneous access route to the jugular vein, the implantation 1 in this case being provided in the inferior vena cava (it will be noted that access could also be provided by exposing the vein).

When a thin metal guide cable has been introduced via the access route provided (jugular vein, then superior vena cava and, finally, inferior vena cava) and the access route aperture through the skin has been widened slightly, the operator can fit an assembly formed of a relatively rigid mandrel and an outer sheathing 19 made of biocompatible material to the proximal end of the cable (which then emerges from the jugular vein).

When the sheathing and mandrel have reached the implantation area in the vessel 21, the cable and the mandrel can be withdrawn.

Thus positioned, the sheathing 19 is used as a guide for positioning the device 1 which is usually already in the state in which its fingers are radially folded (and then extend substantially parallel to one another along the axis 3) in a sort of packaging syringe such that they can easily be introduced inside the sheathing, from its proximal end 19a which, it will be appreciated, emerges on the exterior of the surface marked 23 of the patient's skin.

In order to reach the distal end 19b of the sheathing, the device 1 (entraining behind its looped thread 15 passing through the thin control catheter 17) is urged by a hollow pusher member 25, through which the thin tube 17 passes, as can be clearly seen in FIG. 5.

Once the device 1 has reached the end 19b of the sheathing, it naturally expands elastically, its fingers 7 spreading out radially owing to their flexibility, bearing against the inner wall of the vein, being secured by means of the hooks 11.

The operator can then remove the sheathing 19 and, if necessary, pull on the ends 15a, 15b of the thread 15 by maneuvering the tube 17 in order to tighten the fingers 7 to which the thread 15 is thus connected. Thus, the filter is operational and, it will be appreciated, receives the blood flowing towards it, the direction of which is shown by the arrow 27 in FIG. 6, the blood passing through the structure at the point where the passages separate the fingers 7.

In order to avoid leaving the proximal end 17a of the tube 17 emerging from the patient's skin, the operator can provide a small subcutaneous housing 29 in which he can place this tube end, after altering its length and securing the emerging end of the thread 15 by a knot 31, for example, holding the fingers of the device in question in the close-together, filtering position. The operator can crimp an olive-shaped ovoidal part 32 about the catheter for the purposes of marking.

Once the assembly has been concealed in the housing, the operator can close the access route such that the assembly is trapped beneath the skin, after suture, as shown in FIG. 7.

The filter can, for example, be left in this way for a fortnight, or even a month or longer, until the cardiovascular risk necessitating its fitting has been eliminated.

At this point, it is sufficient for the practitioner to remove the "olive" 32 from its housing, remove the securing device from the thread 15 and pay it out by pulling the tube 17 towards him, if necessary, in order to relieve the stress exerted on the fingers in question which are close together until this point and which then unfold naturally, completely opening the device which then adopts its natural shape again, shown in FIG. 2.

The blood can then pass freely through the device which no longer acts as a filter.

If the practitioner then considers it appropriate (and in particular if it will subsequently be necessary for the device to act as a filter again), he can simply place the olive 32 and thread 15 back in their housing and close the access route with a suture, as shown in FIG. 7.

It will be appreciated that different alternative embodiments of the invention can be envisaged.

Thus, firstly, all the tips of the fingers 7 could be connected together at one end, the thread then passing through as many loops 13.

It would also be possible to make one V-shaped finger of each two of a shape-memory alloy, for example a thermal shape-memory alloy, such as "Nitinol" (registered trademark), which is an alloy based on approximately 50% titanium and 50% nickel.

Thus, by the effect of thermal stress, it would be possible to develop the shape of the device from its conical or frustoconical filtering position to its non-filtering position in which all the fingers are spaced apart.

The memory alloy used could, for example, be stressed thermally, by means of a catheter 34 inserted from the exterior and bringing to the "filtering cone" (which would be the state in which the device is implanted) a heating or cooling fluid 35 (such as a physiological serum), causing the cone to open and consequently freeing the vessel (see FIG. 9).

A further solution for changing from the filtering position to the non-filtering position and vice versa, once the device has been implanted, would be to use a long, relatively flexible cable 37 terminating at each end in a loop 39, 41, the two ends 15a, 15b of the looped thread 15 passing through both loops and through those loops 13 of at least some of the fingers 7, such that, from beyond the loop 39 and by remote-control, the fingers can be pulled and drawn close together or released and moved apart (see FIG. 10).

In the above, the structure of the vascular implantation 1 is thus arranged so as to have a series of lines connected by curved end portions, and it can thus elastically adopt a first, implanted position in which it is folded under stress and in which the zigzag lines extend axially substantially adjacent one another, and a second, radially unfolded position in which these same lines are spaced apart from one another at an angle so as to define the tubular surface with a diameter adapted to the receiver vessel.

Alternatively, it is still possible to provide for the zigzag lines to be sinuous instead of rectilinear, using a plurality of metal wires. It is also possible to envisage fingers or blades parallel with the axis 3 of the implantation device 1, joined in pairs of fingers, one finger being joined to the adjacent finger, by sinuous spring blades connected at one axial end to a finger and at the opposite axial end to the adjacent finger, a tie acting on one finger of each pair and enabling the fingers to be moved close to the axis 3 so as to form the filtering cone.

An implantation which, on the interior, has the shape of an hour-glass in the filtering position (with two conical areas head-to-tail) is also conceivable.

Thus, it is not so much the zigzagged shape of the fingers which appears a priori to be the essence of the invention as the possibility of obtaining permanently, when the device is implanted, firstly an open surface with a tubular wall which efficiently stabilises this device along the axis of the vessel and, secondly, the possibility of locally deforming this open surface to form a constriction area of variable geometry, the blood passing between the "openings" in the surface and only the clots being retained.

I claim:

1. A blood filter device adapted to be implanted inside a blood vessel, comprising:
    a strand formed in a zigzag configuration including
        an endless series of elongated sections being joined
        by bends at opposite ends of said filter device to form, upon uniform full expansion, an essentially cylindrical open wall;

tie means linked to fewer than all said bends, at one of the opposite ends of said filter device, for variably constricting those strand sections to which the tie means are linked, thus forming an essentially frusto-conical/conical open wall for engaging said blood vessel, the constricted strand sections axially converging for controllably filtering encountered blood clots flowing through the filter device.

2. The filter device set forth in claim 1 further comprising:

retaining means attached to the strand and adapted to penetrate the blood vessel for anchoring the filter device within the vessel.

3. The filter device set forth in claim 1 wherein:

said bends to which the tie means are linked have loops;

said tie means comprising a tie passing through said loops.

4. A blood filter device adapted to be implanted inside a blood vessel, comprising:

a strand formed in a zigzag configuration including an endless series of elongated sections being joined by bends at opposite ends of said filter device to form, upon uniform full expansion, an essentially cylindrical open wall;

an elongated tie passing through loops present at fewer than all said bends at one of the opposite ends of said filter device;

said tie passing through opened operating means, located adjacent the loops for permitting the tie to be pulled with alterable tightness, resulting in corresponding changeable constriction of said one end of the filter device, thus forming an essentially frusto-conical/conical open wall for engaging the blood vessel, the constricted strand sections axially converging for variably filtering encountered blood clots flowing through the filter device.

5. The filter device set forth in claim 4 further comprising:

retaining means attached to the strand and adapted to penetrate the blood vessel for anchoring the filter device within the vessel.

6. A blood filter device adapted to be implanted inside a blood vessel, comprising:

a strand formed in a zigzag configuration including an endless series of elongated sections being joined by bends at opposite ends of said filter device to form, upon uniform full expansion, an essentially cylindrical open wall;

preselected pairs of connected elongated sections being made of memory alloy to allow differential thermally induced expansion of the preselected pairs as compared with the remaining strand sections between a first position in which said preselected pairs are constricted at one of said opposite ends, thus forming an essentially frusto-conical/conical open wall for engaging said blood vessel, the constricted strand sections axially converging for filtering encountered blood clots therein, and a second position in which said preselected pairs are expanded at said one end of the filter device, thereby forming a generally essentially cylindrical wall allowing unrestricted blood flow therethrough.

7. The filter device set forth in claim 6 further comprising:

catheter means located in the blood vessel, adjacent the filter device, for introducing a fluid, of preselected temperature, into the vessel for thermally stressing the memory alloy and causing the differential thermally induced expansion.

8. A method for implanting a variable blood filter device into a blood vessel, comprising the steps:

shaping a strand into a zigzag configuration including an endless series of elongated sections being joined by bends at opposite ends;

linking tie means with fewer than all said bends, at one of the opposite ends of said filter device;

variably constricting those strand sections to which the tie means are linked, to form an essentially frusto-conical/conical open wall for engaging said blood vessel, the constricted strand sections axially converging for controllably filtering encountered blood clots flowing through the filter device; and selectively displacing the constricted strand sections, in situ, to form a generally essentially cylindrical wall allowing unrestricted blood flow therethrough.

9. The method set forth in claim 8, wherein the steps of selectively displacing the constricted strand sections further comprises:

loosening the tie means to allow radial expansion of the constricted strand sections.

10. A method for implanting a variable blood filter device into a blood vessel, comprising the steps:

shaping a strand into a zigzag configuration including an endless series of elongated sections being joined by bends at opposite ends of said filter device, preselected pairs of connected elongated sections of said strand being made of memory alloy to allow differential thermal induced expansion of the preselected pairs as compared with the remaining elongated sections;

implanting said strand into said blood vessel;

introducing a fluid of preselected temperature into the blood vessel, in the vicinity of the filter device, thus causing said differential thermally expansion of the preselected pairs, between a first position in which said preselected pairs are constricted at one of said opposite ends, thus forming an essentially frusto-conical/conical open wall for engaging said blood vessel, the constricted strand sections axially converging for controllably filtering encountered blood clots flowing through the filter device, and a second position in which said preselected pairs are expanded at said one end of the filter device, thereby forming a generally essentially cylindrical wall allowing unrestricted blood flow therethrough.

* * * * *